(12) United States Patent
Cerofolini (10) Patent No.: US 8,273,026 B2
(45) Date of Patent: Sep. 25, 2012

(54) ULTRASONIC IMAGING METHOD AND PROBE FOR 3D GYNAECOLOGIC INSPECTION

(75) Inventor: Marino Cerofolini, Subbiano (IT)

(73) Assignee: Esaote, S.p.A., Milan (IT)

( * ) Notice: Subject to any disclaimer, the term of this patent is extended or adjusted under 35 U.S.C. 154(b) by 1339 days.

(21) Appl. No.: 11/334,286

(22) Filed: Jan. 18, 2006

(65) Prior Publication Data

US 2006/0241452 A1 Oct. 26, 2006

(30) Foreign Application Priority Data

Jan. 18, 2005 (EP) .................................. 05100286

(51) Int. Cl.
*A61B 8/00* (2006.01)
(52) U.S. Cl. ...................... 600/443; 600/437; 600/447
(58) Field of Classification Search .................. 600/441, 600/437, 443–447; 128/916
See application file for complete search history.

(56) References Cited

U.S. PATENT DOCUMENTS

| 4,398,422 A | 8/1983 | Haerten et al. |
| 5,070,879 A | 12/1991 | Herres et al. |
| 5,085,221 A | 2/1992 | Ingebrigtsen et al. |
| 5,460,179 A | 10/1995 | Okunuki et al. |
| 6,572,548 B2 * | 6/2003 | Cerofolini ...................... 600/443 |
| 6,582,372 B2 * | 6/2003 | Poland ............................ 600/463 |
| 6,671,227 B2 * | 12/2003 | Gilbert et al. .................. 367/138 |
| 6,824,514 B2 * | 11/2004 | Poland et al. .................. 600/437 |
| 7,156,812 B2 * | 1/2007 | Seward et al. ................. 600/466 |
| 2007/0088213 A1 * | 4/2007 | Poland ........................... 600/437 |

FOREIGN PATENT DOCUMENTS

EP 0432771 6/1991

* cited by examiner

*Primary Examiner* — Brian Casler
*Assistant Examiner* — Christopher Cook
(74) *Attorney, Agent, or Firm* — Woodard Emhardt Moriarty McNett & Henry LLP (57) ABSTRACT

An ultrasonic imaging method particularly for 3D gynaecologic inspections provides an ultrasound probe having a number of transducers forming a linear array. An imaging scanning unit connected to the transducers alternatively generates electric driving signals for each transducer. The probe is oscillated in a direction transversal to the longitudinal extension of the linear array of transducers and around an axis coinciding or parallel to the longitudinal extensions of the linear array of transducers to modify the orientation of the direction of propagation of the ultrasound signals. The ultrasound beams are steered so that the linear array of transducers generates a trapezoidal scanning slice or plane diverging in the direction of propagation of the beams.

7 Claims, 8 Drawing Sheets

Fig. 1

Prior Art

Fig. 8 though the axis of oscillation of the probe is not coincident with the central longitudinal axis of the linear array.

ULTRASONIC IMAGING METHOD AND PROBE FOR 3D GYNAECOLOGIC INSPECTION

CROSS-REFERENCE TO RELATED APPLICATION

The present application claims the benefit of European Patent Application Serial No. 05100286.3, filed on Jan. 18, 2005, which is hereby incorporated by reference in its entirety.

BACKGROUND

The invention relates to an ultrasonic imaging method and apparatus and in particular, to an ultrasound imaging method and apparatus for 3-D gynaecologic inspections.

Linear arrays of transducers in which the transducers are placed side by side along a straight line generate images which are corresponding to a scanning plane perpendicular to the transducer frontal emitting and receiving surfaces and in which the dimension in the longitudinal direction of the transducer array is constant for the entire scanning depth. Thus the images obtained are essentially of a rectangular shape.

Convex linear arrays of transducers produce an image having a trapezoidal shape, the dimension of the imaged area and thus of the image obtained increasing with the depth of penetration of the scanning pulse within the target body.

When an oscillating transducer array is provided, it is important that the axis of oscillation is coincident as far as possible with the longitudinal central axis of the array. This is done in order to reduce as far as possible vibrations to the probe due to the oscillating mass. Also, the requested power for oscillating the array of transducers is reduced when the axis of oscillation is very near or coincident with the central longitudinal axis of the array.

With convex linear arrays, the axis of oscillation can be a secant of the array or can be coincident with a line connecting the two ends of the array or even the axis of oscillation could be chosen as to be tangent to the central point of the convex linear array. Thus there are always parts of the array having a considerable radial distance from the axis of rotation which induces considerable angular momentums. Under this condition the power needed for oscillating the convex or arched array is greater than in the plane rectilinear array and thus the probe is subjected to considerable vibrations. In addition, due to the energy law of conservation, the free orientation of the probe, particularly relative to an axis of angular displacement not parallel to the axis of oscillation of the array of transducers, is hindered so that the manipulation of the probe becomes more difficult or uncomfortable.

The above mechanical effect is far from being a negligible detail since it has to be considered that the oscillation is an alternative motion. So the direction of motion of the array of transducers has to reversed each time. This requires deceleration and acceleration of the mass of the transducer. Furthermore the kinetic energy is very high since the frequency of oscillation is very high, particularly when a very high frame rate is desired. According to the above the motor for driving the array of transducers has to furnish sufficient power for rapidly stopping and accelerating the array to a certain speed; consequently the effects of the mechanical inertia on the entire probe form the point of view of the vibrations and of the reduced handiness of the probe are considerable.

A further drawback in using a so called convex array of transducers, that is, an array of transducers aligned along an arched line such that the emission surfaces of the transducers are placed with the axis perpendicular to the emission surfaces oriented along the radial direction of the curved line and away from the centre of curvature, is that the trapezoidal surface covered by the convex array of transducers is very wide so that often problems arises of acoustic coupling in some areas of the said surface.

In gynaecologic imaging, for example of the fetus, the width of the rectangular imaged zone obtained by a normal linear array of transducers is not sufficient in order to image the entire region, particularly at high penetration depths at which at least part of the fetus is located. A trapezoidal imaged area diverging in the direction of penetration of the emitted ultrasound beams would be more suited for the ultrasound fetal examination so that a convex probe would be the better one to be applied. Nevertheless using such a convex probe would cause the drawbacks indicated above if it is desired to carry out a 3-D (three dimensional) image acquisition.

SUMMARY

An object of the disclosure is to provide for an ultrasonic imaging method and apparatus for 3-D gynaecologic inspections which can overcome the drawbacks of the actual state of the art by allowing a wider field of view or imaged region, particularly a trapezoidal image region in combination with an automatic oscillating array of transducers having very limited inertial effects on the probe and reducing the problem of acoustic coupling in the marginal areas of the imaged region.

A further object of the present invention is to provide for an ultrasound probe which particularly adapted to carry out the above mentioned method.

Still another object of the present invention is to provide an ultrasound imaging system particularly suited for carrying out the above mentioned method.

The invention achieves the above mentioned aims by means of an ultrasonic imaging method for 3-D gynaecologic inspections of the kind in which a linear ultrasound probe is provided having a certain number of transducers which are placed side by side along a line. A B-mode imaging scanning unit is connected to the transducers and alternatively generates electric driving signals for each transducer of the probe in order to excite the transducers to emit ultrasound transmission signals and to receive the electric signals generated by each transducer due to the excitation of the transducers by the ultrasound signals reflected from a target body against which the ultrasound transmission signals have been emitted. A starting orientation is defined for the direction of propagation of the ultrasound transmission signals and for the ultrasound reflected signals, along which a first scanning step is carried out. The probe is oscillated in a direction transversal to the longitudinal extension of the linear array of transducers and around an axis coinciding or parallel to the longitudinal extensions or coinciding or parallel to the central longitudinal axis of the linear array of transducers in order to modify the orientation of the direction of propagation of the ultrasound transmission signals and of the ultrasound reflected signals. A scanning step is carried out along each new oriented direction of propagation corresponding to a different oscillation angle of the probe. A 3-D scan-converter is provided in which the received signals relating to the ultrasound reflected signals are stored. A B-mode image producing means is provided that generates and stores an image from the received signals relating to the ultrasound reflected signals. The B-mode image is then visualized on a monitor screen. The ultrasound emitted beams are steered so that the linear array of transducers generates a trapezoidal scanning slice or plane diverging in the direction of propagation of the beam. The reflected beam signals are focussed to generate a trapezoidal image corresponding to the steered ultrasound beams.

The characteristics of the disclosure and the advantages derived therefrom will appear more clearly from the following description of non limiting embodiments, as illustrated in the annexed drawings.

DESCRIPTION OF THE EMBODIMENTS

As it is known to the skilled person, each transducer of an array of transducers generates upon excitation an ultrasound pulse which propagates from the surface of the excited transducer. By exciting the different transducers of the array to emission of the corresponding ultrasound pulse at different instants it is possible to focus the beams emitted by the array of transducers along a certain line. The excitation delays among different transducers of an array define the line and the orientation of the line along which the single pulses emitted by the single transducers constructively interfere so that a focalization on the line is obtained.

By applying certain delays rules it is possible to focus the emitted ultrasound beams on a line which is diverging laterally outside the slice or surface that is defined by a perpendicular projection of the longitudinal extension of the array of transducers, such that the emitted ultrasound beams cover two triangular zones outside the typical rectangular image zone of a linear array of transducers. Obviously in order to generate an image, the same focussing rule must be applied for the reflected beams.

Thus using a linear array of transducers it is possible to virtually generate a trapezoidal image similarly to a convex array of transducers while avoiding the drawbacks relating to the oscillation of a convex array of transducers and the drawbacks of acoustic coupling problems of a convex array of transducers.

Figure 1:
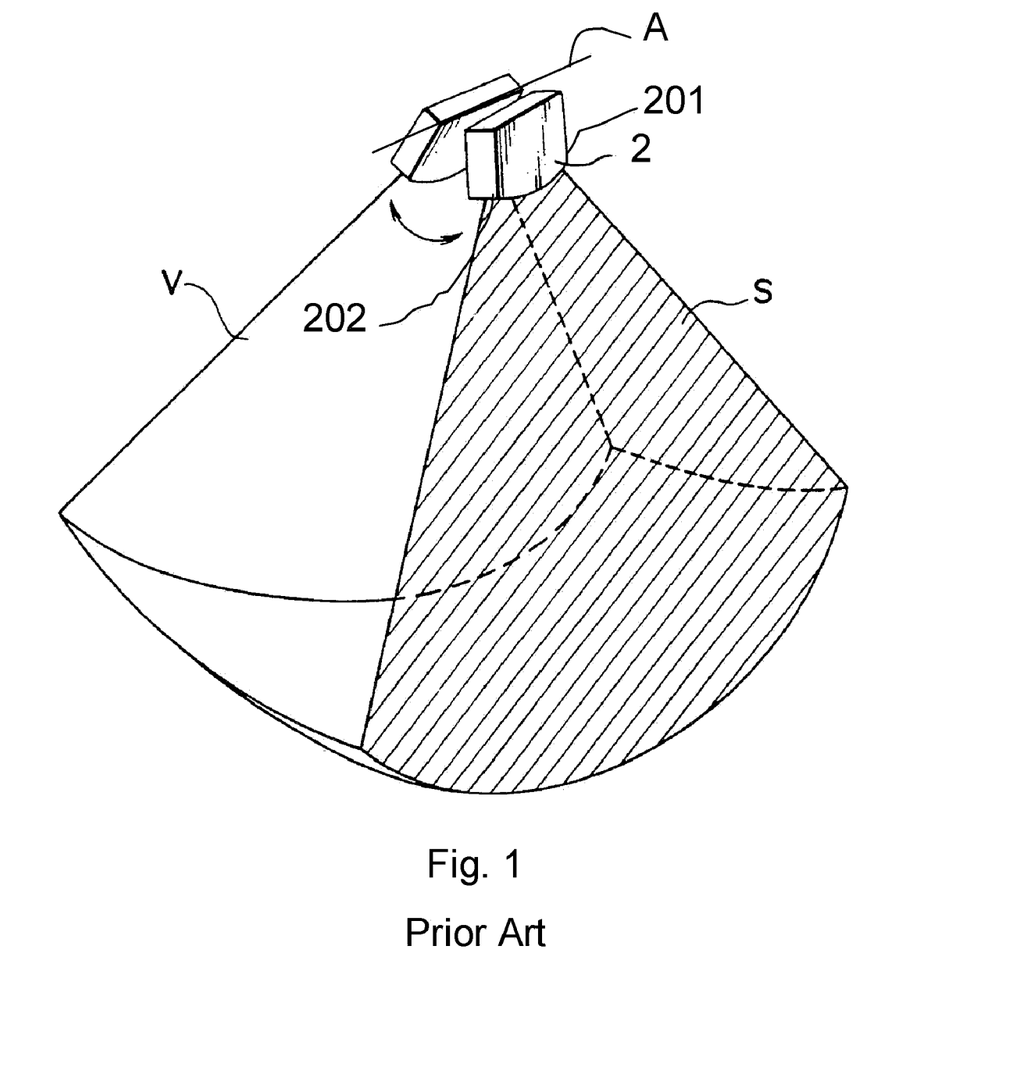
FIG. 1 is a schematic view of a trapezoidal shaped scanned slice of a convex probe.
Figure 2:
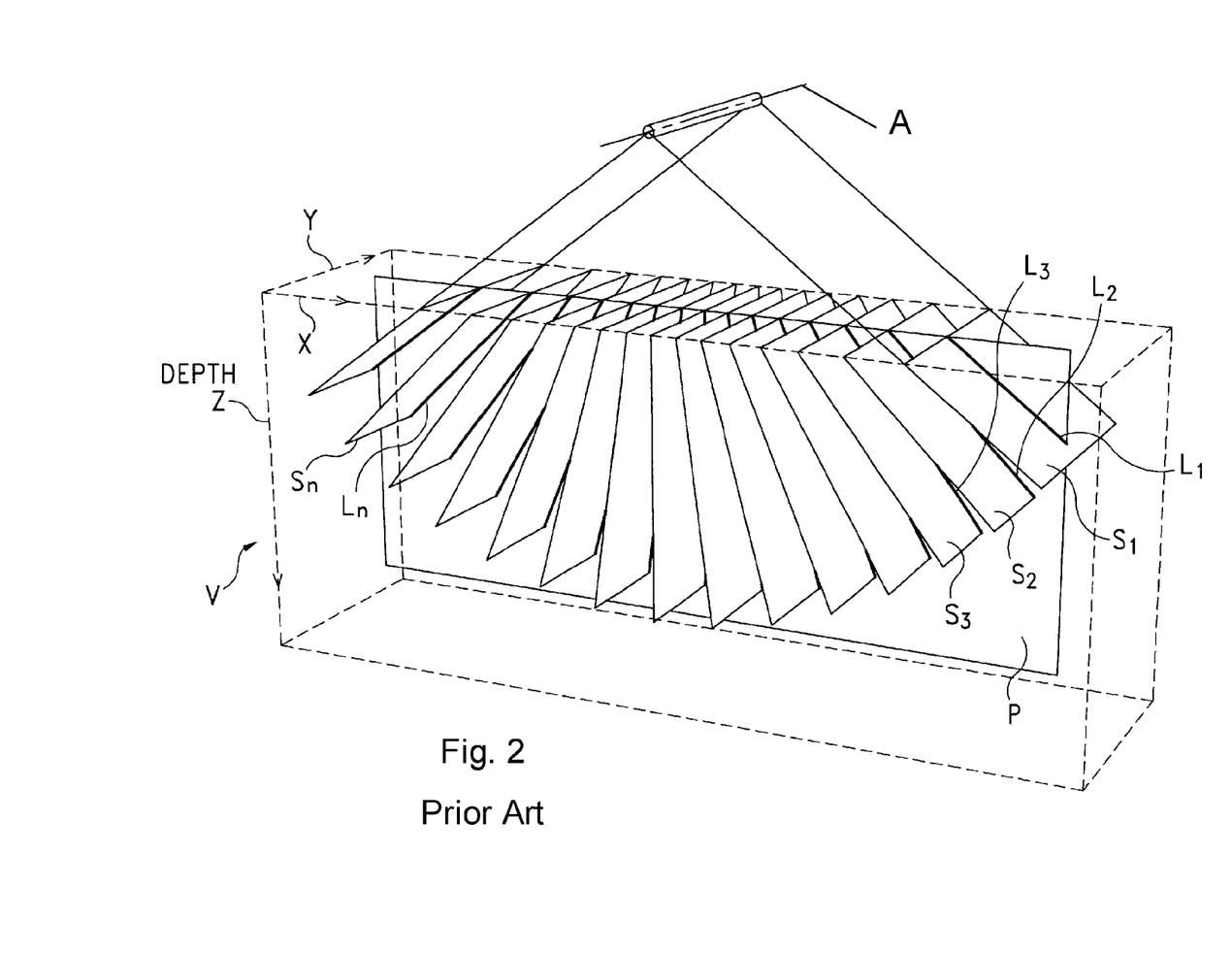
FIG. 2 is a schematic view of a rectangular shaped scanned slices of a linear probe.
Figure 3:
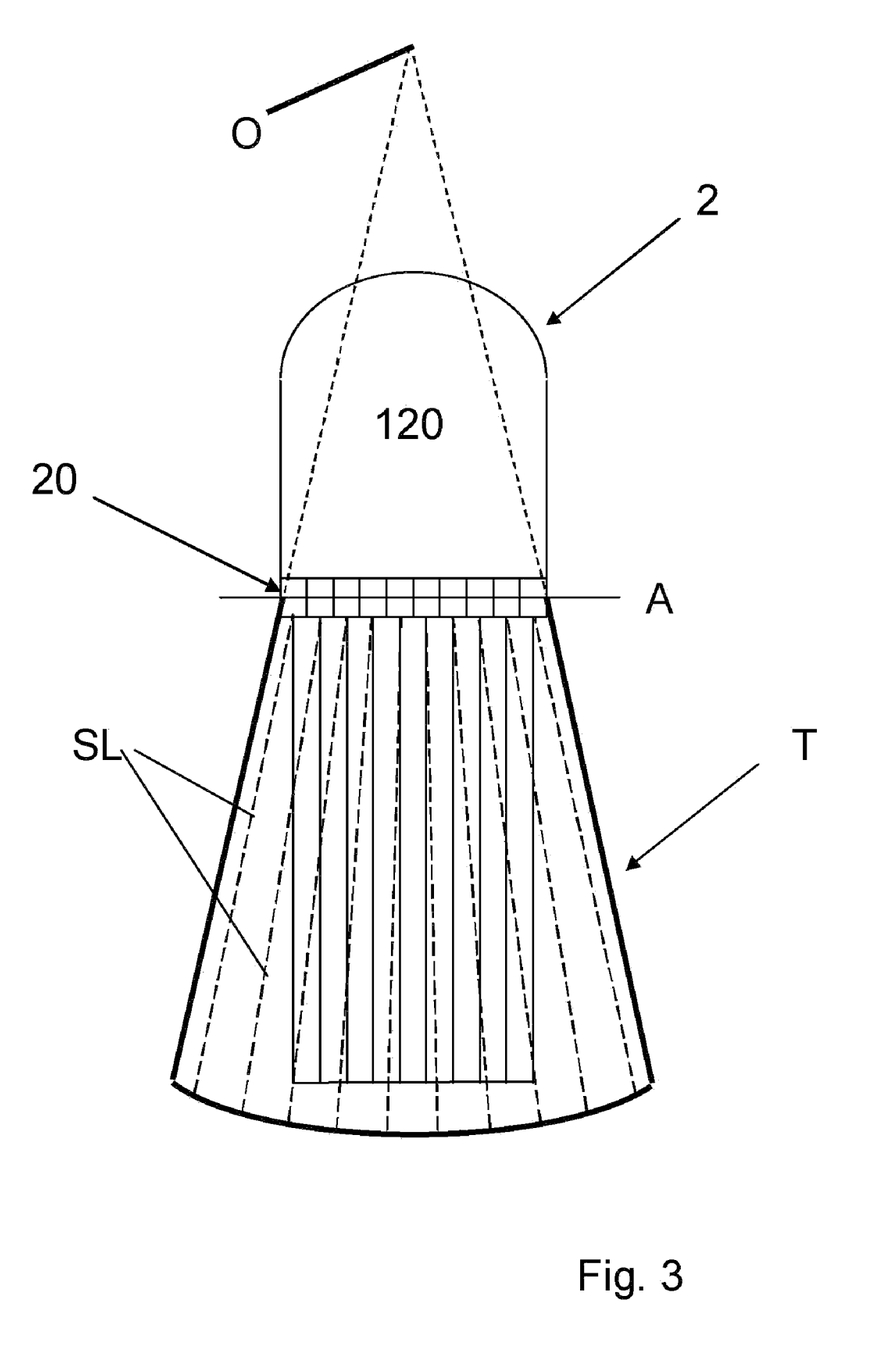
FIG. 3 is a schematic view of a trapezoidal scanned slice of a linear array probe according to an aspect of one embodiment.

FIGS. 1 and 2 illustrate a typical trapezoidal image area of a convex probe and of a linear probe, while FIG. 3 illustrates a trapezoidal image area obtained by a beam steering step provided according the method of the disclosure.

The steering of ultrasound emitted beams can be obtained as known to the skilled person by providing transducer driving signals having delays in driving each transducer of the array so that the emitted ultrasound beams are laterally steered outwards of the lateral limits of the imaged area defined by the projection of the linear array of transducers in a direction perpendicular to the longitudinal extension of the said linear array. Although U.S. Pat. No. 5,447,158 discloses a method of steering ultrasound beams emitted by a linear probe in such a way as to obtain a trapezoidal scanning or image area, applying steering as a solution to the problem of improving a 3-D ultrasound imaging method and system in order to overcome the drawbacks of a 3-D ultrasound convex probe is not considered.

In accordance with an embodiment of the disclosure, an ultrasound probe incorporates a linear array of ultrasound transducers, i.e. an array of transducers arranged side-by-side along a straight line and supported in such a manner as to swing about an axis which is parallel to the straight line along which the transducer array extends, and which axis is near or passes through the center of mass of the array of transducers. On or near this axis is provided an electric motor which controls the oscillation of the transducer array through a drive. The electric motor and the drive for oscillating the transducer array are housed inside a probe case. The probe case includes a housing having an end portion which is sealed and in which the linear transducer array and the drive are housed, and a housing for accommodating and allowing the passage of connecting wires and the motor with the two housings being separated from each other in a liquid-tight manner. A liquid-tight passage for the connecting wires and the motor shaft from one housing to the other is provided.

With reference to the trapezoidal scanning planes obtained by laterally steering the ultrasound beams, it has to be highlighted that in the present disclosure the scanning on the trapezoidal scanning plane is not obtained by steering the ultrasound beams in order to have inclined parallel ultrasound beams, but the trapezoidal scanning plane is covered by carrying out scanning along a number of adjacent scanning lines which are not parallel but are angularly displaced one from the other and are oriented along different angular directions relatively to a common center of angular displacement on which center falls the prolongations of the scanning line in a backward direction relative to the propagation direction.

Furthermore the disclosure provides an ultrasound imaging system particularly suited for carrying out the above mentioned method including in combination an ultrasound probe including a linear array of transducers which is swingable around an axis being parallel to or coincident with the longitudinal axis of the linear array of transducers. An ultrasound image scanner is coupled to the probe for scanning a slice of the interior of a target body having a trapezoidal shape. An ultrasound image producer produces image data from the reflected ultrasound scanning beams and displays the image data on a display device.

The ultrasound image scanner may include means for steering the ultrasound beam formed by the contribution of the emitted ultrasound pulses of each of the transducers of the linear array of transducers so that the surface or slice scanned by the ultrasound beam has a trapezoidal shape having an increasing width in direction of propagation of the ultrasound beams.

This steering means may also include means for generating a sequence of time delayed excitation pulses of the single transducers so as to cause the transducers to emit time delayed ultrasound pulses that are determined in such a way as to generate ultrasound beams focused on propagation directions which sweep the trapezoidal slice.

The steering means may be formed by a transmission beamformer which is driven by a control unit according to a selected time delay sequence of the transducers excitation pulses. This sequence can be retrieved from a time delay sequence memory. Several time delay sequences may be stored in the memory which can be selected by selection input means.

The image producer may include a receiver beamformer which reconstructs the contributions of the single transducers in accordance with the time delay sequence and which feeds a scan converter which generates the image data.

Further image processing units can be provided before feeding the image data to a monitor on which the image data is displayed as an image.

Alternatively to a three dimensional scan converter, such as is described in U.S. Pat. No. 6,572,548, different devices and technique can be used to generate an image resembling a three dimensional image. For example, image data of each scanning plane can be stored on a slice by slice basis, with each slice being defined by a scanning plane, in which the stored image data of each slice or scanning plane is indexed by means of polar coordinates such that the origin of is the common axis of oscillation of the scanning planes. After storing, a rendering may be carried out by using the image data and after the rendering operation is carried out a conversion of the image data in Cartesian coordinates can be executed in order to view or print the images on a display. These operations can be carried out in order to obtain a three dimensional rendering in real time.

The method disclosed in U.S. Pat. No. 6,582,372 utilizes a probe in conjunction with little or no specialized 3-D software/hardware to produce images having depth cues to create the illusion of depth.

The advantages of the method and apparatus of the present disclosure will be described as follows. FIG. 1 illustrates the volume V which is canned by a so called convex array probe in which the probe 2 or only the array of transducers is oscillated around an axis A which is parallel to the axis connecting the two ends of the array 201, 202. By swinging the probe or the array of transducers a share of trapezoidal slices of the target body are scanned. The slices S have a trapezoidal shape with an arched basis.

As it appears clearly from FIG. 1, there are always segments of the array which will have a certain radial distance from the axis of oscillation event if the axis A passes through the centre of mass of the convex array.

Figure 7:
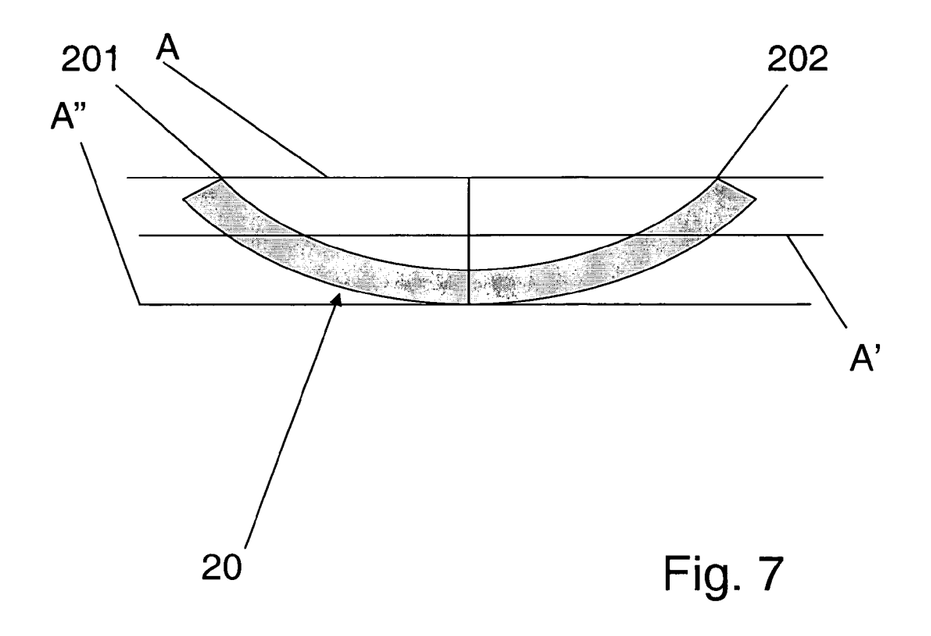
FIG. 7 illustrates a lateral view of a convex array of transducers showing several possible positions of an axis of oscillation.

FIG. 7 illustrates schematically a convex array of transducers 20 and three possible axis of oscillation A, A', and A". Axis A connects the two end points 201, 202. Axis A' passes through the centre of mass and the third axis A" is tangential to the central point of the array of transducers. It is evident that for each position of the axis of oscillation there a large section of the array and thus a large number of transducers that are radially displaced from the axis, thus contributing to a great mechanical inertia.

FIG. 2 illustrates a condition in which a three dimensional linear transducer array is used. In this case the array is made of transducers aligned side by side in a row along a straight line. Thus the axis of oscillation A will have always the same radial distance from each part of the array or from each transducer. More precisely said, the axis of oscillation passing the centre of mass of the array will pass through the centre of mass of each transducer element due to the limited radial dimensions of the cross section of the linear array. The volume scanned by a 3-D linear array probe, namely a probe or an array which is oscillated around an axis of oscillation A passing through the centre of mass of the array and parallel to the longitudinal axis of the said linear array, is formed by a series of differently oriented rectangular shaped scanning planes or slices indicated by S1, S2, S3, . . . Sn. Thus the scanned area or volume has a constant width all over the penetration depth Z in the body under examination. In FIG. 2 the intersection of the scanning planes is shown with an image plane P oriented in the x-z plane as defined by the Cartesian system x, y, z. The intersection lines of the scanning planes with the image plane are indicated with L1, L2, L3, . . . Ln. The image plane can have any orientation in the three dimensional space and due to the fact that a three dimensional volume is scanned by means of the scanning planes S1 to Sn, such that any plane can be used in order to generate an image of the body under examination along the chosen image plane.

FIG. 3 illustrates schematically a probe 2 having a linear array 20 of transducers 120. Each transducer can be excited by an electric excitation signal separately from the other transducers to emit an ultrasound pulse. Furthermore each transducers can be excited by the reflected ultrasound beams impinging on it to generate a corresponding electric signal which is then elaborated in order to extract the information in the form of image data.

By exciting each transducer with an excitation signal having a predetermined certain delay with respect to the excitation of the preceding transducer in the array, the emitted pulses of the transducers of the array interfere in such a way as to generate a beam B having a certain direction and location on the scanned slice. Thus a scanning beam can be generated which sweeps a slice having a trapezoidal form diverging in the direction of propagation of the ultrasound beams, i.e. in the direction of penetration of the scanned slice in the examined body.

Small dotted lines are the scanning lines on which the ultrasound beams are focused by steering. This scanning lines diverge laterally outwardly from a rectangular slice defined by the projection of the linear array in a direction perpendicular to its longitudinal extension.

Analogously, large dotted lines are the scanning lines on which the ultrasound beams are focused by steering the beams in the opposite direction. The axis or oscillation of the linear array of transducers is indicated by A.

It is evident that by oscillating the array of transducers to which the above mentioned steering law is applied, a scanning volume can be obtained which has an intermediate shape as the one of FIG. 1 and FIG. 2.

Figure 4:
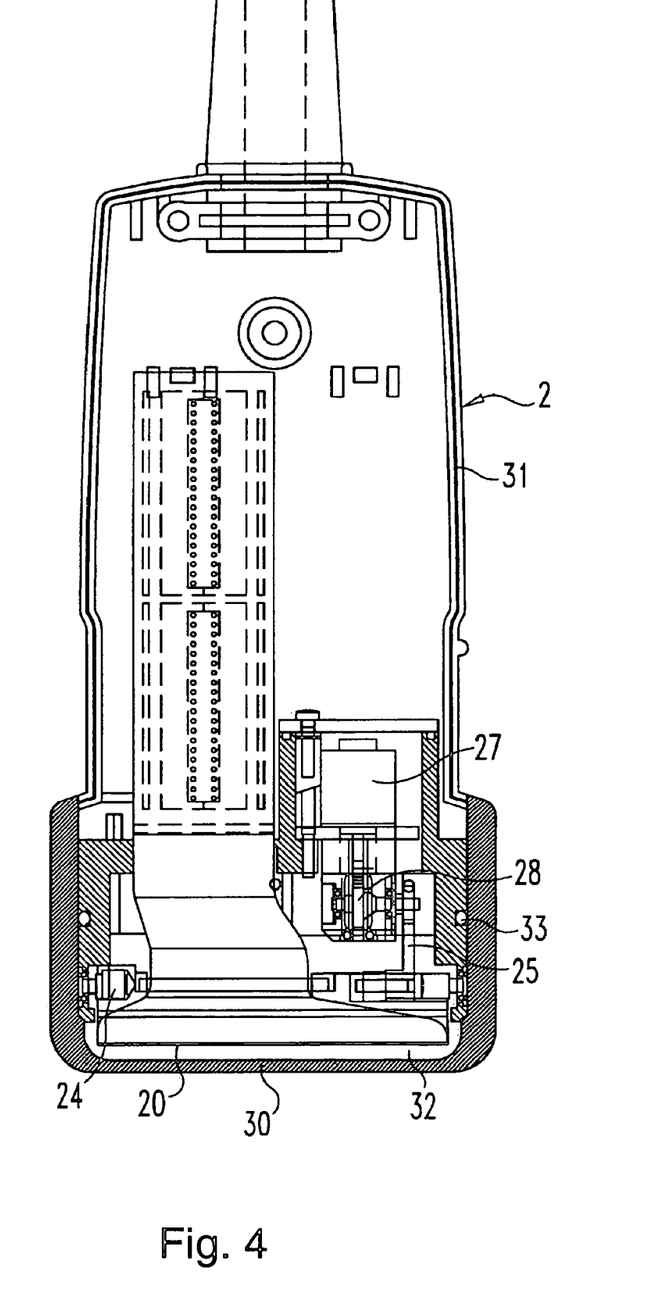
FIGS. 4 and 5 are two sectional views with respect to two different perpendicular planes of a 3-D linear probe type according to an aspect of one embodiment.
Figure 5:
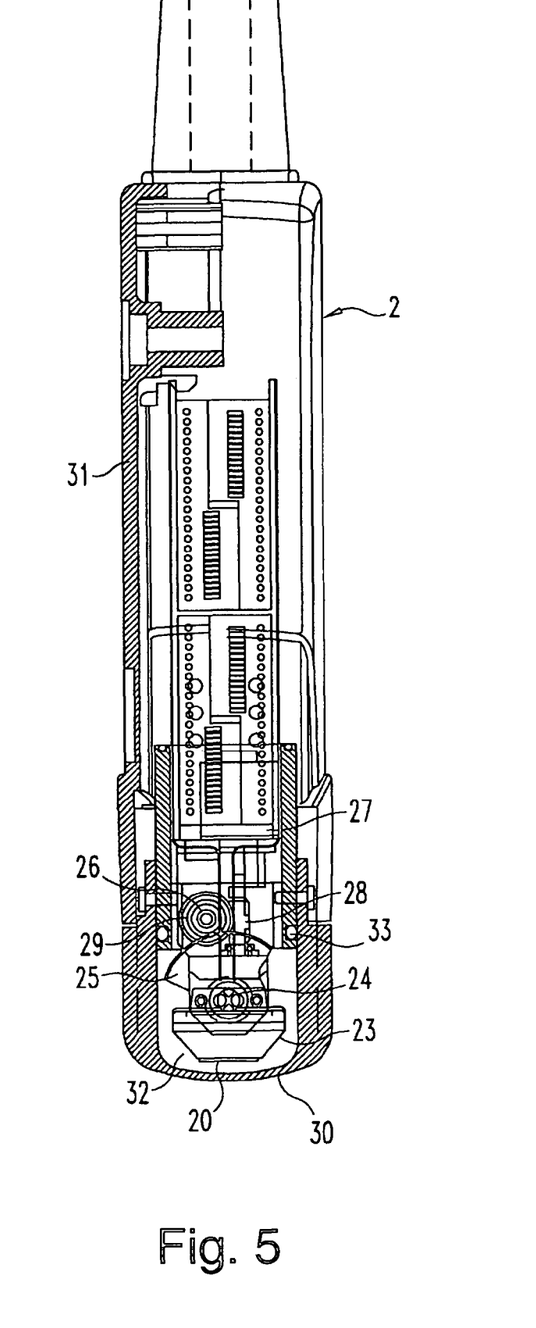

In FIGS. 4 and 5 an example of a so called linear sector probe is illustrated. This probe includes a transducer array 20 for performing a two-dimensional scan, i.e. a scan following a plurality of lines, named lines of view, or beams, named sector beams, oriented parallel or substantially parallel to the probe axis and arranged side-by-side to cover a whole predetermined section plane of the object volume.

The transducer array 20 is mounted inside a housing of a support 23 at an end of the probe. The support is mounted in such a manner as to swing about an axle 24 parallel to the extension of the scan planes. The swing axle 24 is provided as near as possible to the centre of mass of the transducer array 20 and at a certain distance from the transmission surface of the transducer array. The swinging support 23 has a toothed circular sector, i.e. a circular rack 25 on the side diametrically opposite to the axle 24, which circular rack 25 cooperates with a pinion 26. The pinion 26 is rotatably driven by a stepper motor 27 through a drive consisting of a gear 28 splined to the motor shaft and a worm 29. The transducer array is outwardly covered by a cap 30 which is connected to the rest of the probe body, formed by a case for accommodating the connecting wires 31, the stepper motor 27 and the drive with the pinion 26 and the circular rack 25. The housing 32 for accommodating the transducer array, the support for the transducers and the circular rack, as well as the drive, is filled with an acoustic coupling liquid which is known and widely used in the art.

The cap has sealing means, such as an o-ring 33, for contact with the rest of the probe body, and in the passage contained in the housing 32 for the stepper motor shaft and the connecting wires of the transducer array.

The transducers are arranged side-by-side along a line and are electronically activated by the control processor to generate an ultrasonic beam, whose focusing point is displaced, by appropriately activating the individual transducers arranged in a straight line, along a line parallel to the straight line wherein the transducers are arranged.

Hence, for each angular position of the transducer array, the plane oriented in the ultrasonic beam transmission direction and parallel to the line wherein the adjacent transducers are arranged is scanned.

This process is repeated for each of the predetermined angular positions of the transducer array, whereby a succession of scan planes is obtained which covers the whole extension of the object volume, as shown in FIG. 3. Essentially, each scan plane consists of a set of lines of view along which the transmitted ultrasonic beam is focused at a certain depth or distance from the surface of the transducers, the focusing rule remaining the same for each line of view. Each scanning line SL of the trapezoidal scanning plane T along which the ultrasound transmission beam is focused is oriented along a direction which is angularly displaced from the direction of the adjacent scanning lines by considering a common center of angular displacement at which the backwards prolongations of the scanning lines intersects and which centre lies in a backward shifted position with respect of the probe head from which the ultrasound waves are transmitted and/or received.

The position of the swing axle of the probe is chosen in such a way that the mechanical momentum and thus inertia is reduced to a minimum and that the transmission plane of the transducers 20 is maintained at a substantially identical distance between the transducers and the facing wall of the covering cap 30 at each angular position of the transducer array.

Figure 6:
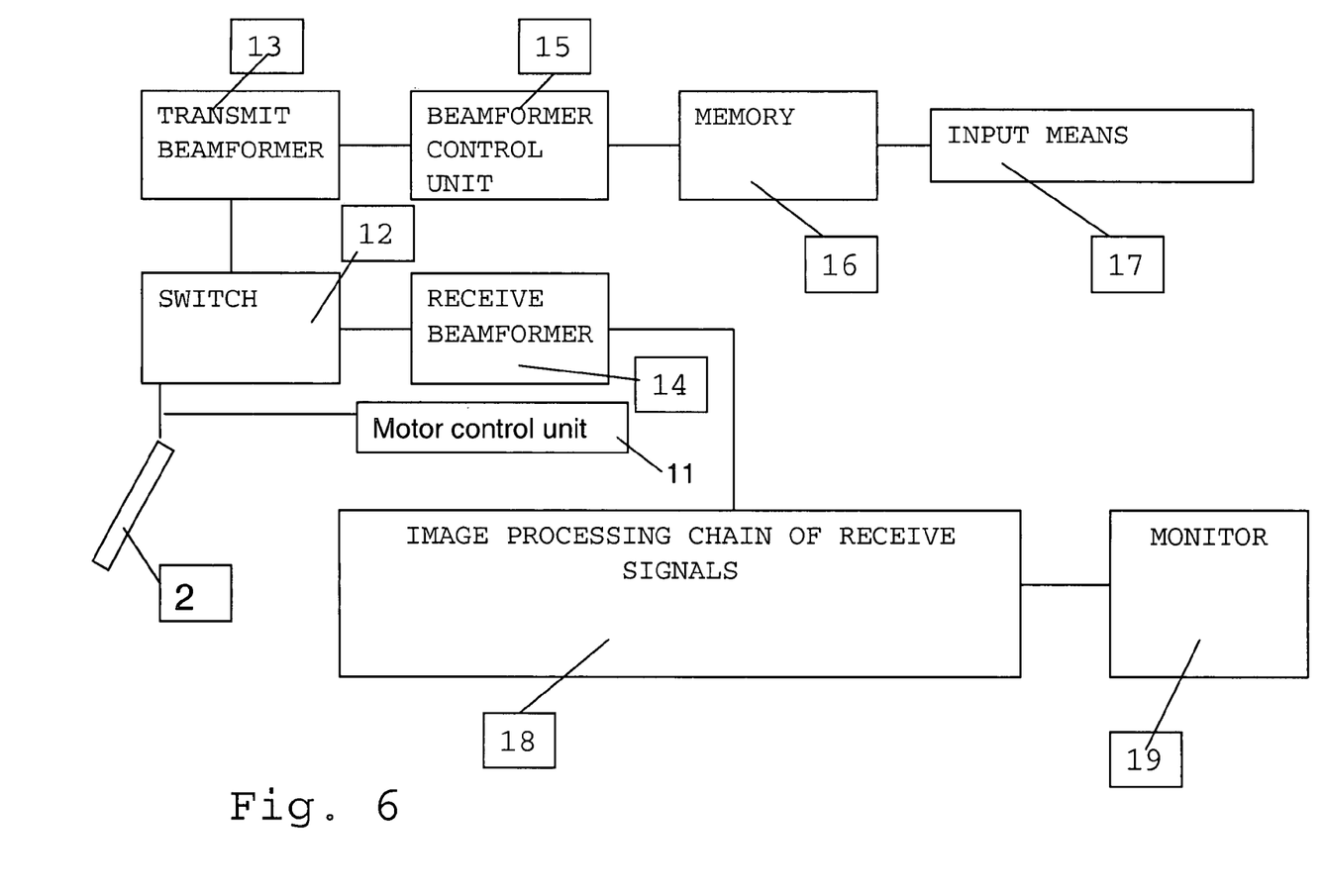
FIG. 6 is a schematic block diagram of an ultrasound imaging system according to one embodiment.

FIG. 6 illustrates a simplified block diagram of a ultrasound imaging system comprising the above mentioned probe and designed for carrying out the method of the present disclosure.

The probe 2 is connected by means of a switch 12 respectively to a transmit beamformer 13 and to a receive beamformer 14. The probe is also connected to a motor control drive 11.

A beamformer control unit 15 generates the electric excitation signals for each transducers with a predetermined frequency pattern. This signal is fed to the transmit beamformer 13 together with the information relating to the time delays for generating a sequence of time delayed excitation of the single transducers of the transducer array of the probe. This information is furnished by a memory 16 in which a series of different time delay sequences of the excitations of the single transducers of the array are stored in order to generate ultrasound beams focused along certain lines. This different time delay sequences also comprises sequences corresponding to different degrees of steering the ultrasound beams so to obtain different diverging trapezoidal scan planes. These different trapezoidal scan plane steering options can be obtained by an input or selection 17.

In FIG. 6, input or selector 17, shown as a single element, can be formed as a combination of different devices or elements, such as, for example, an input line for accessing the memory and storing therein time delay sequences which have been prepared in a remote system and a user friendly selector which allows the user to simply select one of the beamforming sequences of excitation of the transducers of the array corresponding to a desired trapezoidal steering of the scanning plane generated by the probe.

Figure 8:
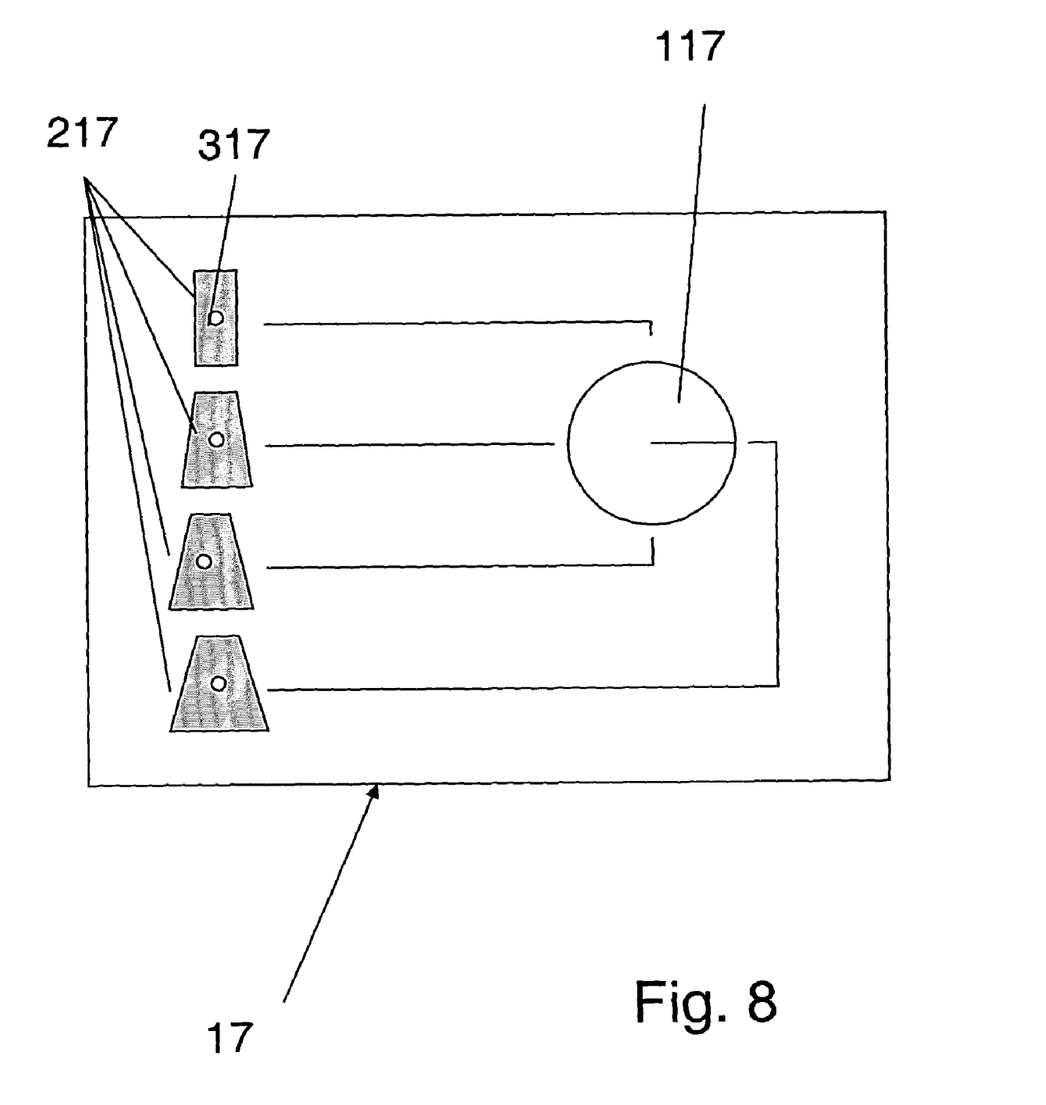
FIG. 8 illustrates a schematic view of a selector unit for choosing steering sequences of an ultrasound probe in order to obtain a trapezoidal scanning plane.

In FIG. 8 a simple selector is illustrated. A rotatable selector knob can be rotated in several angular positions, each position corresponding to the selection command of a certain sequence of excitation of the transducers of the array corresponding to a desired trapezoidal steering of the scanning plane generated by the probe among the ones stored in the memory 16. Each position is related to a scanning plane shape which is indicated by means of an icon 217. Each icon 217 can be associated to a light signal which is activated when the corresponding sequence of excitation pulses is selected. In the illustrative example of FIG. 8, four different scanning plane shapes can be selected starting from the rectangular to the maximum diverging trapezoidal shape of the scanning plane and providing two intermediate less diverging trapezoidal shapes.

Obviously the selector can have other constructive forms as the one illustrated in the example. The selection knob could be avoided by providing a slider or electronic pads. As a variant it is also possible to provide a continuous selection instead of a stepwise selection.

Returning to the system of FIG. 6, the received reflected ultrasound beams are transformed in electric signals by the transducer array. The switch 12 allows transmission of the received echo electric signals generated by the transducers to a receipt beamformer 14 and the signals are then sent to an image data producing chain globally indicated by 18 where this data is finally visualized on a monitor or/and stored on a storage media. The image data producing chain 18 is well known to the skilled person and is not the object of the present disclosure. Normally it includes a scan converter and one or more software/hardware image processing sections for optimising the feature extraction or highlighting from the image data. In the present case since the probe is illustratively shown as a three dimensional scanning probe in the form of a linear array sector probe, the scan converter will be a 3-D scan converter, for example, a 3-D scan converter such as that described in U.S. Pat. No. 6,572,548.

During an image acquisition session the stepped motor of the probe collects image data along each one of several scanning planes so as to cover an entire three dimensional region of interest within the body under examination. Although a linear array probe is used, the scanning plane are essentially of the form according the ones generated by the convex array of FIG. 1. This image data can be acquired by the linear array sector probe avoiding the disadvantages of a convex array sector probe.

By providing input or selection means which enable the user to define the trapezoidal shape and/or the dimensions of this trapezoidal shape of the scanning plane, two options are possible. Referring to the above described method which can be carried out with a selector as illustrated in FIG. 8 the method provides the steps of generating at least two or more different sequences of time delayed excitation pulses of the transducers of the linear array of transducers with each of the said sequences corresponding to a differently steered ultrasound beams and to different trapezoidal shapes; selecting one of the generated sequences of time delayed excitation pulses according to one preferred shape and/or dimension of the trapezoidal scanning plane; and applying the selected sequence of time delayed excitation pulses to the transducer for at least part or all of the scanning planes having different angular orientations.

Alternatively or in combination a continuous variation of the shape and or of the dimensions of the scanning plane can be obtained by an algorithm for generating different sequences of time delayed excitation pulses of the transducers of the linear array of transducers as a function of the geometrical parameters of the shape and/or of the dimension the trapezoidal scanning plane. In this case the input means 17 inputs the parameters of shape and dimension of the scanning plane according to a continuous scale of value of the parameters. The algorithm or the program is carried out in the beamformer control unit 15 by generating the sequence of time delayed excitation pulses of the single transducers 120 that lead to the desired shape and dimension of the scanning plane.

Although the example described is illustratively directed to a B-mode imaging mode, it should be clear that the present method probe and system can be used in combination with other kinds of existing and widely used ultrasound imaging modes, such as for example, harmonic imaging, pulse inversion or other known ultrasound imaging modes.

According to a further improvement of the present disclosure, the image data relative to each scanning plane is stored by identifying the data by means of the index of angular displacement of the said scanning plane with reference to the other scanning planes. A further index indicates the scanning line within the scanning plane. A correlation of scanning lines between the different scanning planes can be provided in order to generate an image from a weighted linear combination of the image data obtained along each of the correlated scanning lines of the different scanning planes. Rendering of this weighted linear combination generates rendering images simulating a three dimensional effect due to the consideration in the image of the weighted image data of the correlated scanning lines in the other scanning planes. The resulting 3-D image presents a viewing angle as though the viewer were directly in front of the slice and at an infinite distance. The front slice (defined to be the one with the highest weighting) is most prominent, while the slices behind the front slice are faded, which gives the cue of depth to the viewer by creating a dimming effect. A structure in the scanned medium which crosses lateral line boundaries and extends back in the elevation dimension will appear to fade back in the distance the farther it is from the front slice. Because the simple rendered view in accordance with the present disclosure is an orthographic projection, it does not include any scaling for depth perspective. That is, structures further from the front slice will not be scaled smaller as they would be in a real 3-D view. Because of this distortion, the total depth and thus the total number of slices should be limited so that the image has a high width-to-depth ratio. This has been referred to as a "clamshell" 3-D image. In a typical 3-D ultrasound scan, even rendered with perspective and arbitrary views, a limited amount of depth information can be recognized and processed by the mind of the user. Accordingly, images presented in accordance with the present disclosure may provide just as much recognizable depth component as fully rendered 3-D images.

This kind of rendering can be done in real time and frame by frame. When considering time in the rendering, a so called four-dimensional image can be viewed on the monitor, representing a three-dimensional time varying image.

What is claimed is:

1. An ultrasonic imaging method comprising the steps of:
providing a linear ultrasound probe comprising a plurality of transducers which are placed side by side along a line forming a linear array;
providing a B-mode imaging scanning unit to which said transducers are connected and which alternatively generates electric driving signals for each of said transducers of said probe for exciting said transducers to emit ultrasound transmission signals and to receive electric signals generated by each of said transducers due to the excitation of said transducers by ultrasound reflection signals reflected from a target body against which said ultrasound transmission signals have been emitted;
defining a starting orientation of the direction of propagation of said ultrasound transmission signals and of said ultrasound reflection signals along which a first scanning step is carried out;
carrying out said first scanning step by emitting said ultrasound transmission signals and receiving said ultrasound reflection signals along the said starting orientation of said direction of propagation;
oscillating said probe in a direction transversal to the longitudinal extension of said linear array of transducers and around an axis coinciding or parallel to said longitudinal extensions or coinciding or parallel to a central longitudinal axis of said linear array of transducers for modifying the orientation of said direction of propagation of said ultrasound transmission signals and of said ultrasound reflection signals;
carrying out additional scanning steps along each new oriented direction of Propagation corresponding to a different oscillation angle of said probe;
providing a 3-D scan-converter in which received signals related to said Ultrasound reflection signals are stored;
providing B-mode image producing means for generating an image from said received signals related to said ultrasound reflection signals; characterized by the steps of:
steering said ultrasound transmission signals so that said linear array of transducers generates a trapezoidal scanning plane diverging in the direction of propagation of said transmission signals;
carrying out scanning along a number of adjacent scanning lines which are not parallel but are angularly displaced one from the other and are oriented along different angular directions relative to a common center of angular displacement on which common center fall the prolongations of the scanning line in a backward directions relative to the propagation direction;
providing a reflection signal focusing rule which generates a trapezoidal image corresponding to said steered ultrasound signals, wherein said ultrasound transmission signals is obtained by providing transducer driving signals having time delays for driving each of said transducer of said array so that said ultrasound transmission signals are focused on a laterally inclined propagation line deviated outwards from lateral limits of an imaged area defined by the projection of said linear array of transducers in a direction perpendicular to a longitudinal extensions of said linear array;
creating at least two different sequences of time delayed excitation pulses of said transducers of said linear array of transducers, each of the said sequences including differently steered ultrasound transmission signal and at least two scanning planes corresponding to different oscillation angles of said probe and having different shapes or dimensions;
selecting one of said created sequences of time delayed excitation pulses; and
applying said selected sequence of time delayed excitation pulses to said transducers for at least part of said scanning planes having different angular orientations.

2. A method according to claim 1, characterised in that said image data is extracted from said ultrasound reflection signals by harmonic imaging or pulse inversion imaging.

3. An ultrasound imaging system comprising:
an ultrasound probe comprising a linear array of transducers constructed and arranged with an axis of oscillation for position in various angular orientations about said axis of oscillation which is parallel to or coincident with the longitudinal axis of said linear array of transducers wherein each transducer of said linear array is position at the same distance from the axis of oscillation, said transducers generating ultrasound beams;
an ultrasound image scanning means coupled to said probe and responsive to Said ultrasound beams for scanning a slice of the interior of a target body, said slice having a trapezoidal shape and defining a scanning plane, said ultrasound image scanning means comprises a means for steering said ultrasound beams such that the surface of said slice scanned by said ultrasound beams has a trapezoidal shape having an increasing width in the direction of propagation of said ultrasound beams, said ultrasound beams are focused on a laterally inclined propagation line deviated outwards from lateral limits of an imaged area defined by the projection of said linear array of transducers in a direction perpendicular to a longitudinal extension of said linear array,said means for steering said ultrasound beams comprises means for generating a sequence of time delayed excitation pulses for each of said transducer for causing said transducers to emit time delayed ultrasound pulse, the time delays of said excitation pulses being determined in such a way as to generate ultrasound beams focused on different propagation directions which sweep said trapezoidaly-shape slice;
a transmission beamformer connected to said transducers of said probe by means of a switch;
a beamformer control unit for driving said transmission beamformer, said beamformer control unit being coupled to a memory in which at least two sequences of different time delayed excitations pulses of said transducers are stored, or in which an algorithm or program for creating different sequences of differently time delayed excitation pulses of said transducers as a function of geometric parameters of shape or dimensions of said scanning plane is stored, each of the said sequences including differently steered ultrasound transmission signals and at least two scanning planes corresponding to different angular orientations and having different shapes or dimensions;
input means for selecting one of said different sequences of said different time delayed excitation pulses of the transducers, or for inputting shape and/or dimension parameters for said scanning plane;
ultrasound image producing means for producing image data from said ultrasound scanning beams reflected from said target body; and
displaying means for displaying said image data.

4. An ultrasound imaging system according to claim 3, wherein said image producing means comprises a receiver beamformer which reconstructs the contributions of each of said transducers in accordance with said time delay sequences and which feeds a scan converter for generating said image data.

5. An ultrasound imaging system according to claim 4, comprising a plurality of image processing units for generating said image data and feeding said image data to a monitor on which said image data is displayed.

6. An ultrasonic imaging method comprising the steps of:
providing a linear ultrasound probe comprising a plurality of transducers which are placed side by side along a line forming a linear array;
providing a B-mode imaging scanning unit to which said transducers are connected and which alternatively generates electric driving signals for each of said transducers of said probe for exciting said transducers to emit ultrasound transmission signals and to receive electric signals generated by each of said transducers due to the excitation of said transducers by ultrasound reflection signals reflected from a target body against which said ultrasound transmission signals have been emitted;
defining a starting orientation of a direction of propagation of said ultrasound transmission signals and of said ultrasound reflection signals along which a first scanning step is carried out;
carrying out said first scanning step by emitting said ultrasound transmission signals and receiving said ultrasound reflection signals along the said starting orientation of said direction of propagation;
oscillating said probe in a direction transversal to the longitudinal extension of said linear array of transducers and around an axis coinciding or parallel to said longitudinal extensions or coinciding or parallel to a central longitudinal axis of said linear array of transducers for modifying the orientation of said direction of propagation of said ultrasound transmission signals and of said ultrasound reflection signals;
carrying out additional scanning steps along each new oriented direction of propagation corresponding to a different oscillation angle of said probe;
providing a 3-D scan-converter in which received signals related to said ultrasound reflection signals are stored;
providing B-mode image producing means for generating an image from said received signals related to said ultrasound reflection signals; characterized by the steps of:
steering said ultrasound transmission signals so that said linear array of transducers generates a trapezoidal scanning plane diverging in the direction of propagation of said transmission signals;
carrying out scanning along a number of adjacent scanning lines which are not parallel but are angularly displaced one from the other and are oriented along different angular directions relative to a common center of angular displacement on which common center fall the prolongations of the scanning line in a backward direction relative to the propagation direction;
providing a reflection signal focusing rule which generates a trapezoidal image corresponding to said steered ultrasound signals, wherein said steering of said ultrasound transmission signals is obtained by providing transducer driving signals having time delays for driving each of said transducers of said array so that said ultrasound transmission signals are focused on a laterally inclined propagation line deviated outwards from lateral limits of an imaged area defined by the projection of said linear array of transducers in a direction perpendicular to a longitudinal extension of said linear array;
providing an algorithm for creating different sequences of time delayed excitation pulses of said transducers of said linear array of transducers as a function of geometrical parameters of the shape and dimensions of said trapezoidal scanning planes, each of the said sequences including differently steered ultrasound transmission signals and at least two scanning planes corresponding to different oscillation angles of said probe and having different shapes or dimensions;

inputting said parameters of shape and dimensions of said scanning planes according to a continuous scale of the value of said parameters; and applying said created sequence of time delayed excitation pulses to said transducers for at least part of said scanning planes having different angular orientations.

7. A method according to claim 6, characterised in that said image data is extracted from said ultrasound reflection signals by harmonic imaging or pulse inversion imaging.

* * * * *

UNITED STATES PATENT AND TRADEMARK OFFICE
CERTIFICATE OF CORRECTION

PATENT NO. : 8,273,026 B2  
APPLICATION NO. : 11/334286  
DATED : September 25, 2012  
INVENTOR(S) : Marino Cerofolini It is certified that error appears in the above-identified patent and that said Letters Patent is hereby corrected as shown below:

Claim 1, column 10, line 44 please insert --said steering of-- after "wherein" and before "said ultrasound".

Signed and Sealed this  
Thirteenth Day of November, 2012

David J. Kappos  
*Director of the United States Patent and Trademark Office*